(12) United States Patent
Stehle et al.

(10) Patent No.: US 10,282,917 B2
(45) Date of Patent: May 7, 2019

(54) INTERACTIVE MESH EDITING

(71) Applicant: KONINKLIJKE PHILIPS N.V., Eindhoven (NL)

(72) Inventors: Thomas Heiko Stehle, Hamburg (DE); Fabian Wenzel, Hamburg (DE); Carsten Meyer, Hamburg (DE); Lyubomir Georgiev Zagorchev, Burlington, MA (US); Martin Bergtholdt, Hamburg (DE); Jochen Peters, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/577,355

(22) PCT Filed: Jun. 29, 2016

(86) PCT No.: PCT/EP2016/065142
§ 371 (c)(1),
(2) Date: Nov. 28, 2017

(87) PCT Pub. No.: WO2017/001476
PCT Pub. Date: Jan. 5, 2017

(65) Prior Publication Data
US 2018/0158252 A1 Jun. 7, 2018

Related U.S. Application Data
(60) Provisional application No. 62/185,981, filed on Jun. 29, 2015.

(30) Foreign Application Priority Data
Aug. 3, 2015 (EP) .................................. 15179465

(51) Int. Cl.
*G06T 15/08* (2011.01)
*G06T 15/20* (2011.01)
(Continued)

(52) U.S. Cl.
CPC .............. *G06T 19/20* (2013.01); *A61B 6/466* (2013.01); *G06T 15/08* (2013.01); *G06T 15/20* (2013.01);
(Continued)

(58) Field of Classification Search
CPC ... G06T 15/20; G06T 19/003; G06F 3/04815; A63F 13/525–13/5258; A63F 2300/6661–2300/6684
See application file for complete search history.

(56) References Cited

U.S. PATENT DOCUMENTS 6,246,784 B1 * 6/2001 Summers ........... G06K 9/00201
382/128
8,437,579 B2   5/2013 Fradkin et al.
(Continued)

OTHER PUBLICATIONS

Reitinger, Bernhard, et al. "Liver surgery planning using virtual reality." IEEE Computer Graphics and Applications 26.6 (2006).*
(Continued)

*Primary Examiner* — Daniel F Hajnik

(57) ABSTRACT

A system and method are provided for interactive editing of a mesh which has been applied to a three-dimensional (3D) image to segment an anatomical structure shown therein. To facilitate the interactive editing of the applied mesh, a view of the 3D image is generated which shows a mesh part to be edited, with the view being established based on a local orientation of the mesh part. Advantageously, the view may be generated to be substantially orthogonally to the mesh part, or to a centerline of the anatomical structure which is determined as a function of the mesh part. Accordingly, an orthogonal view is established which facilitates the user in
(Continued)

carrying out the editing action with respect to the mesh part. It is therefore not needed for the user to manually navigate through the 3D image to obtain a view which is suitable for mesh editing, which is typically time consuming.

11 Claims, 4 Drawing Sheets

(51) Int. Cl.
  *G06T 19/00*   (2011.01)
  *G06T 19/20*   (2011.01)
  *A61B 6/00*    (2006.01)
  *A61B 34/10*   (2016.01)

(52) U.S. Cl.
  CPC ........ *G06T 19/00* (2013.01); *A61B 2034/105* (2016.02); *G06T 2210/41* (2013.01); *G06T 2219/008* (2013.01); *G06T 2219/028* (2013.01); *G06T 2219/2021* (2013.01)

(56) References Cited

U.S. PATENT DOCUMENTS

| | | | |
|---|---|---|---|
| 9,008,386 B2 | 4/2015 | Verstraeten et al. | |
| 2004/0001110 A1* | 1/2004 | Khan | G06F 3/04815 715/848 |
| 2004/0249270 A1 | 12/2004 | Kondo et al. | |
| 2005/0237324 A1 | 10/2005 | Guhring | |
| 2007/0116335 A1 | 5/2007 | Capolunghi et al. | |
| 2008/0079722 A1 | 4/2008 | Burns et al. | |
| 2008/0118131 A1 | 5/2008 | Skinner et al. | |
| 2012/0136236 A1 | 5/2012 | Roberts | |
| 2013/0051645 A1* | 2/2013 | Kim | G06K 9/00 382/131 |
| 2013/0135305 A1 | 5/2013 | Bystrov et al. | |
| 2013/0328874 A1 | 12/2013 | Smith-Casem et al. | |
| 2015/0011886 A1 | 1/2015 | Radulescu et al. | |

OTHER PUBLICATIONS

Mackinlay, Jock D., Stuart K. Card, and George G. Robertson. "Rapid controlled movement through a virtual 3D workspace." ACM SIGGRAPH computer graphics. vol. 24. No. 4. ACM, 1990.*

Ecabert, O. et al., "Automatic Model-based Segmentation of the Heart in CT Images", IEEE Transactions on Medical Imaging 2008, 27(9), pp. 1189-1201.

Borgo, R. et al., "An easy-to-use visualization system for huge cultural heritage meshes", Virtual Reality, Archeology, and Cultural Heritage, NY, (Nov. 28, 2001), pp. 121-130.

Decle, F. et al., "Tech-note: ScrutiCam: Camera manipulation technique for 3D objects inspection", 3D User Interfaces, IEEE Symposium , NJ, (Mar. 14, 2009), pp. 19-22.

Kitslaar, P.H. et al., "Automated determination of optimal angiographic viewing angles for coronary artery bifurcations from CTA data", Progress in Biomedical Optics and Imaging, SPIE—International Society for Optical Engineering, WA, vol. 6918, (Feb. 17, 2008), pp. 69181J-1.

* cited by examiner

INTERACTIVE MESH EDITING

CROSS-REFERENCE TO PRIOR APPLICATION

This application is the U.S. National Phase application under 35 U.S.C. § 371 of International Application No. PCT/EP2016/065142, filed on Jun. 29, 2016, which claims the benefit of U.S. patent application Ser. No. 62/185,981 and European Patent Application No. 15179465.8, filed on Jun. 29, 2015 and Aug. 3, 2015. These applications are hereby incorporated by reference herein.

FIELD OF THE INVENTION

The invention relates to a system and a method for interactive mesh editing. The invention further relates to a workstation and imaging apparatus comprising the system. The invention further relates to a computer program product comprising instructions for causing a processor system to perform the method.

BACKGROUND OF THE INVENTION

Meshes are frequently applied or mapped to medical images to segment one or more anatomical structures contained therein. Here, the term 'segmentation' refers to the identification of an anatomical structure in the medical image, e.g., by delineation of the boundaries of the anatomical structure, by labeling of the voxels enclosed by the boundaries, etc. Once such segmentation has been performed, it is possible to extract clinical parameters such as, in case of, e.g., a cardiac structure, ventricular volume and wall thickness. Such segmentation is frequently also referred to as delineation or annotation.

An applied mesh or mapped mesh may also be displayed together with the medical image to visualize information, such as the shape and location of the anatomical structure. For example, a mesh may be shown as an overlay to a three-dimensional (3D) medical image such as a Computed Tomography (CT), Magnetic Resonance Imaging (MRI) or Ultrasound (US) image. Such a 3D image may, together with the applied mesh, be visualized in various ways. Therefore, alternative terms for applied mesh may be mapped mesh, fitted mesh, overlaied mesh, or superimposed mesh. Examples of using the applied mesh or mapped mesh for segmenting a three-dimensional (3D) medical image can be found in WO2004047030A2. For example, the 3D image may be visualized by multi-planar reformatting to generate a 2D view intersecting the 3D image and the applied mesh or mapped mesh. In such a 2D view, the mesh may be shown as a contour. Other view generation techniques are known within the field of 3D image visualization, and include volume rendering and maximum intensity projection.

Meshes may be applied or mapped automatically, manually or semi-automatically to a medical image. The automatic or semi-automatic application may involve the use of an adaptation technique, also termed 'mesh adaptation' or 'mesh fitting'. The adaptation technique may, for example, optimize an energy function based on an external energy term which adapts the mesh to the image data and an internal energy term which maintains a rigidness of the mesh. Various adaptation techniques are known for automatically applying meshes to medical images. An example of an automatic technique is described in "Automatic Model-based Segmentation of the Heart in CT Images" by O. Ecabert et al., IEEE Transactions on Medical Imaging 2008, 27(9), pp. 1189-1201, which describes the automatic segmentation of the heart from three-dimensional (3D) Computed Tomography (CT) images.

A previously applied mesh or mapped mesh may require editing by a user. For example, the mesh may be insufficiently accurately applied to serve for diagnostic purposes, generation of normative databases, or generation of ground truth data as input for machine learning algorithms. Such mesh editing may be performed interactively using a view of the 3D image and the applied mesh or mapped mesh which shows a part of the mesh which is to be edited. Such editing may involve, e.g., re-positioning of a mesh part, increasing the resolution of a mesh part, etc.

Disadvantageously, the orientation of the view in the 3D image may be ill-suited for the planned edition action. In conventional image viewing applications, the view orientation may be switched between coronal, sagittal, and transversal orientations. However, this may provide insufficient flexibility for obtaining a suitable view. In some applications, it is possible to interactively reformat the view to an arbitrary orientation, but adapting it on-the-fly to the optimal orientation during mesh editing is prohibitively time-consuming.

SUMMARY OF THE INVENTION

It would be advantageous to have a system or method for interactive mesh editing which automatically provides a suitable view of the 3D image and the mapped mesh.

A first aspect of the invention provides a system for interactive mesh editing, comprising:
an image data interface for accessing image data, the image data representing a three-dimensional image showing an anatomical structure;
a processor configured for:
i) obtaining mesh data, the mesh data defining a mesh which having been previously mapped to the three-dimensional image for segmenting the anatomical structure,
ii) generating a view of the three-dimensional image and said mapped mesh, wherein said generating is based on one or more viewing parameters defining the view, and
iii) generating view data representing the view for display on a display;
a user input interface for receiving user input data indicative of an editing action to be mapped to at least a part of the mesh shown in the view;
wherein the processor is configured for establishing the one or more viewing parameters based on a local orientation of the part of the mesh upon receiving the user input data indicative of the editing action,
wherein the part of the mesh comprises a set of mesh surface elements, and wherein the processor is configured for determining the local orientation of the part of the mesh by applying a statistical function to the normal vectors of the mesh surface elements from the set of mesh surface elements.

A further aspect of the invention provides a workstation or imaging apparatus comprising the system.

A further aspect of the invention provides a method for interactive mesh editing, comprising:
accessing image data, the image data representing a three-dimensional image showing an anatomical structure;
obtaining mesh data, the mesh data defining a mesh which having been previously mapped to the three-dimensional image for segmenting the anatomical structure;

receiving user input data indicative of an editing action to be applied to at least a part of the mesh shown in the view;

generating a view of the three-dimensional image and the mapped mesh, wherein said generating is based on one or more viewing parameters defining the view;

generating view data representing the view for display on a display; and wherein the generating the view comprises establishing the one or more viewing parameters based on a local orientation of the part of the mesh upon receiving the user input data (082) indicative of the editing action.

A further aspect of the invention provides a computer program product comprising instructions for causing a processor system to perform the method.

The above measures involve accessing image data of a 3D image, such as, but not limited to, volumetric image data, a stack of 2D image slices, etc. The 3D image shows an anatomical structure, such as an organ, a part of an organ, tissue, etc. Mesh data is obtained which defines a mesh which has been applied or mapped to the 3D image. For example, the mesh data may define coordinates of mesh surface elements in a coordinate system of the 3D image. As such, the mesh data may provide a segmentation of the anatomical structure. Therefore, alternative terms for applied mesh may be mapped mesh, fitted mesh, overlaid mesh, or superimposed mesh.

A view is generated of the 3D image and of the mesh which has been applied or mapped thereto. As such, the user is shown at least a portion of the 3D image and the applied mesh or mapped mesh. The view is defined by parameters. For example, the parameters may be geometric parameters. A specific example is that the parameters may define a viewing plane through the 3D image which may be used for multi-planar reformatting of the 3D image to generate the view. The view may then be displayed on a display, e.g., in a viewport of an application.

The user may indicate an editing action to be performed in respect of a part of the mesh by providing corresponding user input data. This may involve conventional user interaction techniques, such as, but not limited to, the user operating an onscreen pointer using a pointing device and double clicking on a part of the mesh which is to be edited in an initial view of the 3D image and the applied mesh or mapped mesh, e.g., as shown in a viewport.

In accordance with the above measures, the view parameters for the view are established based on a local orientation of the part of the mesh. Here, the term 'local orientation' refers to an orientation of the part of the mesh within the 3D image, being local in that the orientation represents only that part of the mesh and not the entire mesh.

The above measures have as effect that the local orientation of the part of the mesh which is to be edited is taken into account when generating the view. As such, the view which is generated when receiving the user input data, and which may replace an initial view which was shown at the time the editing action was indicated, may be generated in such a way that it shows the part of the mesh to be edited, and advantageously, provides an optimal view thereof. Namely, the local orientation of the mesh part may be of relevance for enabling the user to carry out the editing action. For example, when increasing the resolution of the mesh part, a 'head-on' parallel view of the mesh part may be desired. However, when seeking to re-position the mesh part, a view which intersects the mesh part orthogonally may be desired so as to allow the user to optimally perform the re-positioning.

Optionally, the processor is configured for establishing the one or more viewing parameters to define the view to intersect the three-dimensional image substantially orthogonally to the part of the mesh, thereby establishing an orthogonal view. The inventors have recognized that a view which orthogonally intersects the part of the mesh to be edited is well suited for many editing actions, such as those which involve re-positioning the part of the mesh. Namely, such re-positioning frequently takes place orthogonally to the mesh due to the mesh locally not sufficiently fitting the anatomical structure, e.g., by being applied 'too narrowly' or 'too widely' around a part of the anatomical structure. An additional advantage of such a view is that, when different adjacent parts of the mesh need to be corrected, the user may further navigate through the 3D image. If the view orthogonally intersects the mesh part, forward navigation or backward navigation typically results in the mesh intersection remaining relatively static within the subsequent navigational views. However, if the mesh is intersected in a very oblique manner, such forward and backward navigation may lead to drastic shifts of the mesh intersection within the navigational views which may be confusing to the user, and/or require considerable mental effort of the user to interpret. It is noted that the term 'substantially orthogonally' may refer to an orthogonal intersection, or one which lies within a narrow range to orthogonal, e.g., +/−5, +/−10, or +/−20 degrees.

Optionally, the processor is configured for, from an initial view showing the part of the mesh, switching to the orthogonal view upon receiving the user input data indicative of the editing action. The orthogonal view may thus be displayed in response to the user indicating his/her desire to perform the editing action.

Optionally, the processor is configured for effecting said switching if the initial view intersects the three-dimensional image parallel to the part of the mesh, or at an intersection angle below a predetermined angle. The view may thus be conditionally switched from the initial view to the orthogonal view, namely only when the initial view is parallel to the mesh part, or intersects the mesh part in an oblique manner, e.g., within +/−10, +/−20, or +/−45 degrees of parallel. As such, a switching of the view may be avoided if the initial view is considered to be non-optimal but adequate for carrying out the editing action.

Optionally, the part of the mesh comprises a set of mesh surface elements, and the processor is configured for determining the local orientation of the part of the mesh by applying a statistical function to the normal vectors of the mesh surface elements from the set of mesh surface elements. Examples of mesh surface elements include triangles, quadrilaterals, etc.

Optionally, the statistical function is an average or a median.

Optionally, the processor may be configured for determining the local orientation of the part of the mesh by determining one or more gray value image gradients of the 3D image at a location where the part of the mesh intersects the 3D image, or in a neighborhood thereof. In general, this may provide an alternative to the use of normal vectors of the mesh surface elements. For example, the gray value image gradients may be determined by determining and evaluating a gray value structure tensor.

Optionally, the set of mesh surface elements is located within a radius of a reference mesh surface element. As such, the statistical function may be applied to a set of surface elements within a radius of a certain reference mesh surface element. The reference mesh surface element may be, e.g., selected by the user, centrally located within the initial view, or may have been determined or identified by the processor in another manner. The radius may be automatically adapted by the processor, e.g., based on a local mesh curvature.

Optionally, the processor is configured for determining a difference between a) a result of the statistical function applied to the normal vectors of the mesh surface elements, and b) the normal vector of the reference mesh surface element, for omitting using the result of the statistical function as said determined local orientation if the difference exceeds a first predetermined threshold. The result of the statistical function is thus only used if the difference with respect to the normal vector of the reference mesh surface element is below a certain threshold. This may be advantageous in certain situations. For example, if the local orientation is determined by averaging the normal vectors, such averaging may misrepresent the local orientation of the mesh part in case the mesh part exhibits a strong curvature, has a complex shape, etc.

Optionally, the processor is configured for, if the difference exceeds the first predetermined threshold:
  determining a subset of the set of mesh surface elements, the subset comprising mesh surface elements of which the normal vector deviates less than a second predetermined threshold from the result of the statistical function; and
  determining the local orientation of the part of the mesh by applying the statistical function to the normal vectors of the mesh surface elements from said subset. The local orientation may thus be determined only based on a subset of mesh surface elements which deviate, in terms of normal vector, less than a certain threshold from the reference mesh surface element. As such, an outlier rejection mechanism may be provided. It is noted that the above steps may be performed iteratively by the processor.

Optionally, the processor is configured for establishing the one or more viewing parameters to define the view to intersect the three-dimensional image substantially orthogonally to a centerline of the anatomical structure which is determined as a function of the location of the part of the mesh. Instead or in addition to orthogonally intersecting a mesh part, the view may also orthogonally intersect a centerline of the anatomical structure which is determined as a function of the location of the part of the mesh. For example, the centerline may be defined as being located in between two sides of the mesh. The processor may thus generate the view to intersect this centerline orthogonally. It is noted that in many cases, this may also result in the mesh part(s) defining the centerline also being intersected substantially orthogonally since the centerline may be defined to be parallel to the mesh part(s).

It will be appreciated by those skilled in the art that two or more of the above-mentioned embodiments, implementations, and/or optional aspects of the invention may be combined in any way deemed useful.

Modifications and variations of the imaging apparatus, the workstation, the method, and/or the computer program product, which correspond to the described modifications and variations of the system, can be carried out by a person skilled in the art on the basis of the present description.

A person skilled in the art will appreciate that the method may be applied to multi-dimensional image data, e.g., to three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the Figures, elements which correspond to elements already described may have the same reference numerals.

List of Reference Numbers

Figure 1:
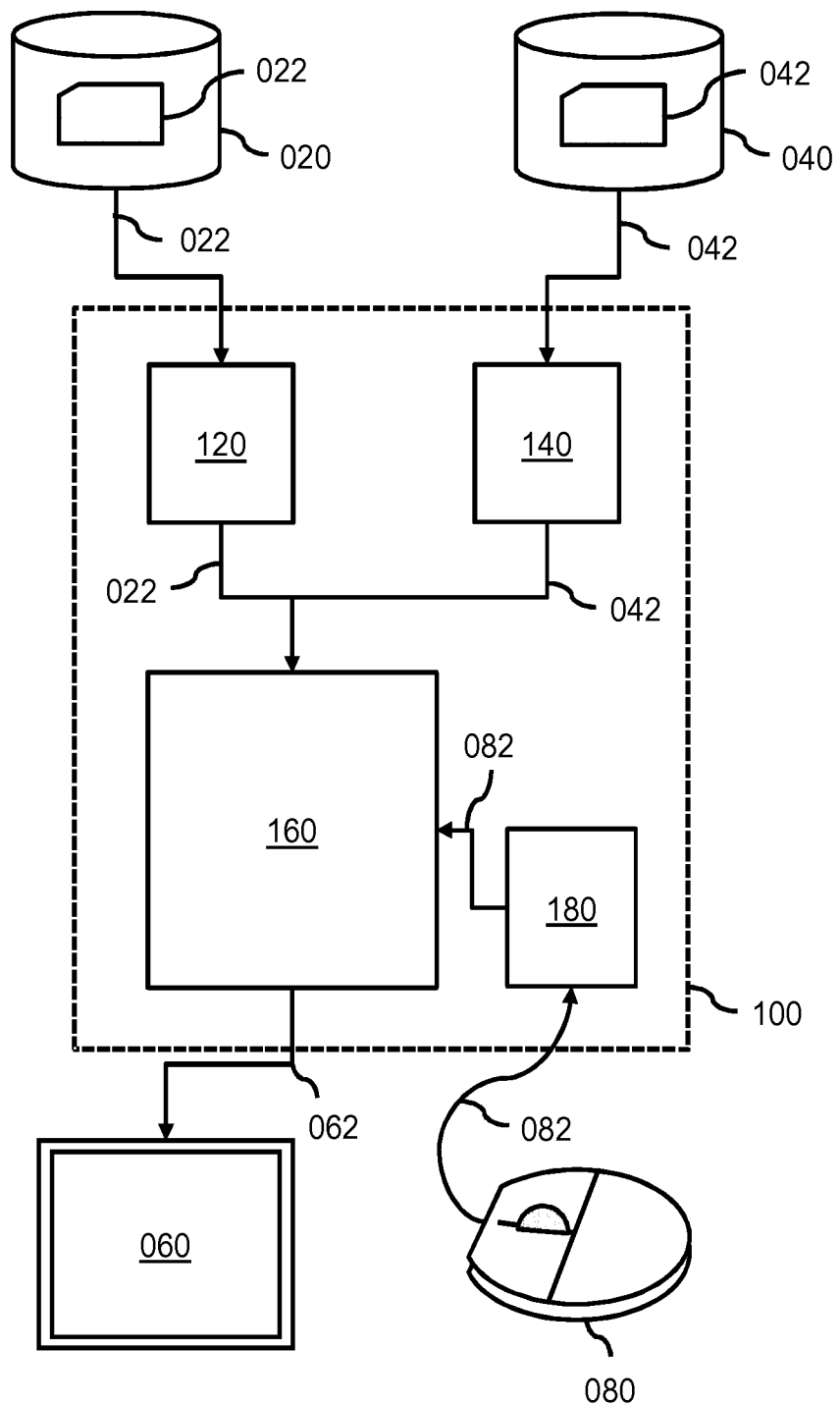
FIG. 1 shows a system for interactive mesh editing, in which a view is generated to intersect the 3D image substantially orthogonally to part of a mesh.

The following list of reference numbers is provided for facilitating the interpretation of the drawings and shall not be construed as limiting the claims.
020 image repository
022 image data of three-dimensional image
040 mesh data storage
042 data defining mesh
060 display
062 view data
080 user input device
082 user input data
100 system for interactive mesh editing
120 image data interface
140 mesh data interface
160 processor
180 user input interface
200, 202 initial view
220, 222 mesh contour
230 part of mesh
232 centerline of anatomical structure
240, 242 orthogonal viewing plane
250, 252 orthogonal view
300 method for interactive mesh editing
310 accessing image data
320 obtaining mesh data
330 receiving user input data 340 generating view
350 generating view data
370 computer readable medium
380 instructions stored as non-transient data

DETAILED DESCRIPTION OF EMBODIMENTS

FIG. 1 shows a system 100 for interactive mesh editing. The system 100 comprises an image data interface 120 for accessing image data 022. The image data may represent a three-dimensional (3D) image showing an anatomical structure. In the example of FIG. 1, the image data interface 120 is shown to be connected to an external image repository 020 which comprises the image data 022. For example, the image repository 020 may be constituted by, or be part of, a Picture Archiving and Communication System (PACS) of a Hospital Information System (HIS) to which the system 100 may be connected or comprised in. Accordingly, the system 100 may obtain access to the image data 022 via the HIS. Alternatively, the image data 022 may be accessed from an internal data storage of the system 100. In general, the image data interface 120 may take various forms, such as a network interface to a local or wide area network, e.g., the Internet, a storage interface to an internal or external data storage, etc. It is further noted that, where applicable, a reference to the 3D image may be understood as a reference to the 3D image's image data 022.

The system 100 further comprises a processor 160 which is configured for obtaining mesh data 042. The mesh data may define a mesh having been previously mapped to the three-dimensional image so as to segment the anatomical structure. In the example of FIG. 1, the processor 160 is shown to obtain the mesh data 042 via a mesh data interface 140 from an external mesh data storage 040. However, the mesh data 042 may also be internally accessed, e.g., from an internal storage such as an electronic memory or disk drive.

The system 100 further comprises a user input interface 180 for receiving user input data 082 indicative of an editing action to be applied to at least a part of the mesh shown in the view. The user input data 082 may be provided by a user device 080 operable by the user. The user device 080 may take various forms, including but not limited to a computer mouse 080, touch screen, keyboard, etc. The user input interface 180 may be of a type which corresponds to the type of user device 080, i.e., it may be a thereto corresponding user device interface.

During operation of the system 100, the processor 160 may generate a view of the three-dimensional image and said applied mesh or mapped mesh, wherein said generating is based on one or more viewing parameters defining the view, and may generate view data 062 representing the view for display on a display 060. The view may be a 2D view, but may equally show depth, e.g., be a 3D view for stereoscopic display on a 3D display. The view data 062 may be output to the display 060, e.g., directly by the processor 160 or via a display output (not shown in FIG. 1). In an example, the generated view may be shown as part of a viewport of an application. To generate the view, the processor may first establish the one or more viewing parameters based on a local orientation of the part of the mesh. For example, the view parameters may be established such that the view intersects the three-dimensional image substantially orthogonally to the part of the mesh, thereby establishing an orthogonal view.

It is noted that various operations of the system 100, including various optional aspects thereof, will be explained in more detail with reference to FIGS. 2A-3B.

The system 100 may be embodied as, or in, a single device or apparatus, such as a workstation or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model.

Figure 2A:
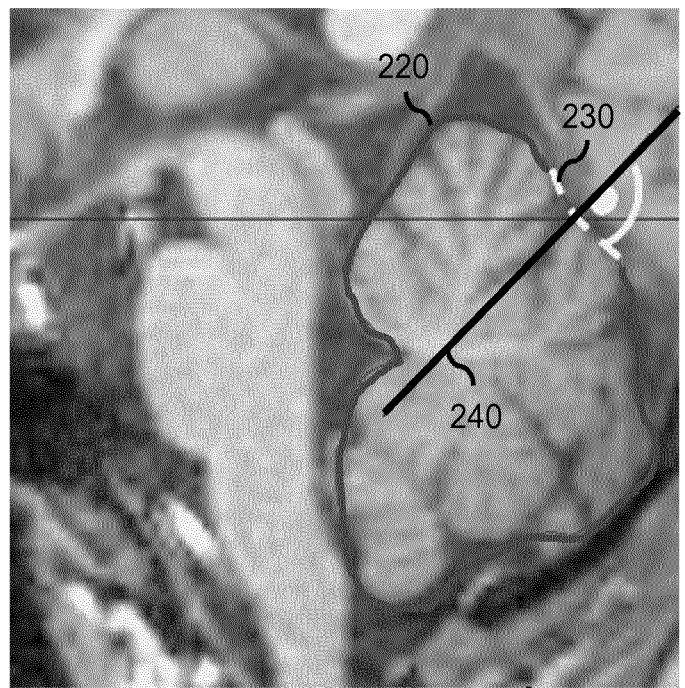
FIG. 2A shows an initial view of a 3D image showing the cerebellum, with a mesh having been applied to the image to segment the cerebellum.

FIG. 2A shows an initial view 200 of a 3D image showing the cerebellum, with a mesh having been applied or mapped to the image to segment the cerebellum. The initial view 200 intersects the 3D image and the mapped mesh 220. As a result, the mapped mesh 220 is shown in the initial view 200 as a contour. The user may desired to edit a part of the mesh, e.g., the mesh part 230 indicated by way of the dashed line. This may be indicated to the system in various ways. For example, the user may activate an editing mode and subsequently select the mesh part 230, e.g., using an onscreen cursor (not shown in FIG. 2A). Another example is that the user may simply activate the editing mode having the mesh part to be edited centrally located within the viewport. The system may thus be informed of the user's intention to edit the mesh part from the user's interaction with the system, i.e., from the user's input.

Figure 2B:
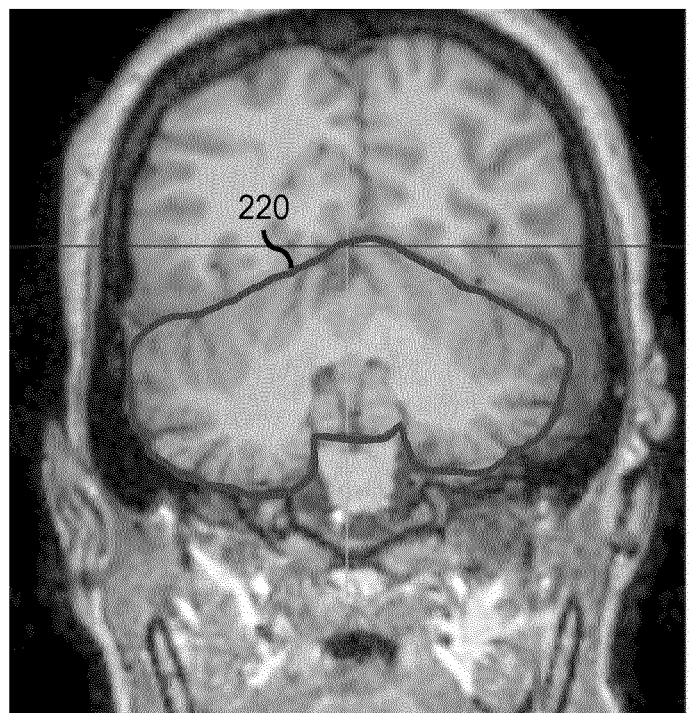
FIG. 2B shows an orthogonal view along a viewing plane as indicated in FIG. 2A, which orthogonally intersects a part of the mesh.

In response to the user's input, the processor may then establish one or more viewing parameters to define a subsequent view which is suitable, or even optimal, for the editing action. In the example of FIGS. 2A and 2B, this may be a view which substantially orthogonally intersects the 3D image at the mesh part 230. The viewing parameters may take various forms. For example, they may define a viewing plane from which the view may be generated. Such a viewing plane 240 is shown in FIG. 2A as a line intersecting the mesh part 230 orthogonally, as indicated by the dot-and-curve symbol. FIG. 2B shows the resulting orthogonal view 250, showing a different contour of the mesh 220. The user may now carry out the editing action based on the orthogonal view 250, e.g., by selecting the mesh part (not explicitly indicated in FIG. 2B) and repositioning it with respect to the 3D image.

Figure 3A:
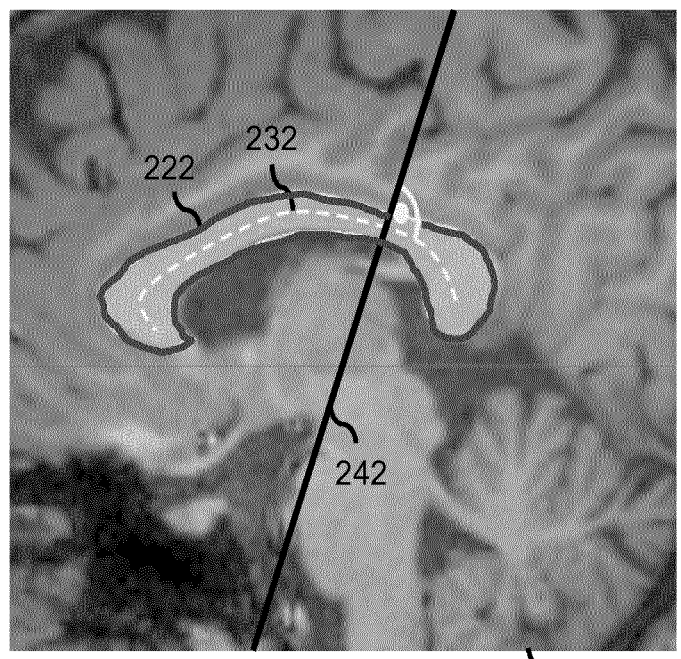
FIG. 3A shows an initial view of a 3D image showing the corpus collosum, with a mesh having been applied to the image to segment the corpus collosum.
Figure 3B:
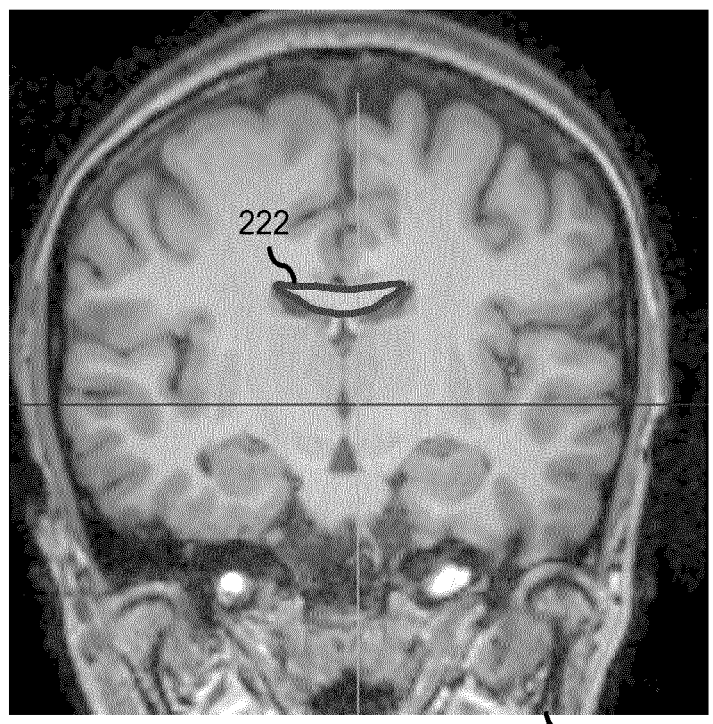
FIG. 3B shows an orthogonal view along a viewing plane as indicated in FIG. 3A, which orthogonally intersects a centerline of the corpus collosum, with the centerline having been determined as a function of the location of at least part of the mesh.

FIGS. 3A and 3B show another example, in which the view is generated to be orthogonal to a centerline of an anatomical structure. Namely, FIG. 3A shows an initial view 202 of a 3D image showing the corpus collosum, with a mesh having been mapped to the image to segment the corpus collosum. The initial view 202 intersects the 3D image, thereby showing a contour of the mapped mesh 222. The user may desire to edit a part of the mesh and may provide user input indicative thereof. In response to the user input, the processor may then establish one or more viewing parameters to define a subsequent view which is suitable, or even optimal, for the editing action. In the example of FIGS. 3A and 3B, this may be a view which intersects the 3D image substantially orthogonally to the centerline 232 of the anatomical structure. The centerline 232 is shown in FIG. 3A as a dashed line, and may be known to the processor. Namely, the centerline 232 may be determined as a function of the location of the mesh 232. A non-limiting example may be that the centerline 232 may be defined as being positioned in between the two lateral sides of the mesh 232.

FIG. 3A further illustrates the established viewing parameters defining viewing plane 242 in the form of a line intersecting the centerline 232 orthogonally, as indicated by the dot-and-curve symbol. In this example, since the two lateral sides of the mesh 222 run substantially parallel to the centerline 232, the viewing plane 242 also intersects said sides of the mesh 222 substantially orthogonally. FIG. 3B shows the resulting orthogonal view 252, showing a different contour of the mesh 222. The user may now carry out the editing action with respect to the orthogonal view, e.g., by selecting the mesh part to be edited (not explicitly indicated in FIG. 2B) and repositioning it with respect to the 3D image.

It will be appreciated that the viewing parameters may take various forms, such as coordinates defining a viewing plane, coordinates defining a virtual camera, parameters defining a volumetric rendering, slice numbers and image coordinates, etc.

It will be appreciated that the local orientation of the part of the mesh may be derived from single mesh surface element, such as a mesh triangle. This may be the case if the mesh part is constituted by a single mesh surface element, or when the single mesh surface element is considered as a reference element for use in determining the local orientation. The local orientation may then be directly determined by the normal vector of the single mesh surface element. Alternatively, as was the case in the example of FIGS. 2A and 2B, when the part of the mesh comprises a set of mesh surface elements, the local orientation of the part of the mesh may be determined by applying a statistical function to the normal vectors of the mesh surface elements from the set of mesh surface elements. For example, the statistical function may be an average or a majority selection, such as a median. The set of mesh surface elements may be defined to be located within a radius of a reference mesh surface element. As such, the processor may determine all mesh surface elements belonging to said set based on a predefined radius and a reference mesh surface element being indicated. The radius may be dynamically determined by the processor, e.g., based on a curvature of the mesh part. For example, the processor may increase the radius for decreasing curvatures, and vice versa.

The processor may further be configured for determining a difference between a) a result of the statistical function applied to the normal vectors of the mesh surface elements, and b) the normal vector of the reference mesh surface element, for omitting using the result of the statistical function as said determined local orientation if the difference exceeds a first predetermined threshold. If the difference exceeds the first predetermined threshold, the processor may determine a subset of the set of mesh surface elements, the subset comprising mesh surface elements of which the normal vector deviates less than a second predetermined threshold from the result of the statistical function, and determine the local orientation of the part of the mesh by applying the statistical function to the normal vectors of the mesh surface elements from said subset.

The following provides a specific but non-limiting example of how the local orientation of the part of the mesh may be determined by the processor. Here, the mesh surface elements are triangles. Firstly, if only one reference triangle is used, its normal vector may be used directly as representing the local orientation. Else, the processor may a) define a radius R in which triangles are to be included in average computation, b) determine triangles that are located within a geodesic distance smaller or equal to R, and c) compute the average $A_v$ of the triangle normal vectors. $A_v$ should not deviate from the reference triangle normal vector more than a threshold $T_1$. If it does, the processor may d) determine triangle normal vectors that deviate from $A_v$ less than a threshold $T_2$, and e) iteratively repeat the procedure c) through d) with the remaining triangles so as to arrive at a stable estimate of the normal vector of the mesh part. Finally, the image volume may be intersected through the selected mesh surface point, perpendicular to the normal vector computed above. A scene camera may then be placed such that its axis coincides with the computed normal vector. That is, its axis may pierce the surface in the selected point and it is parallel to the normal direction.

Figure 4:
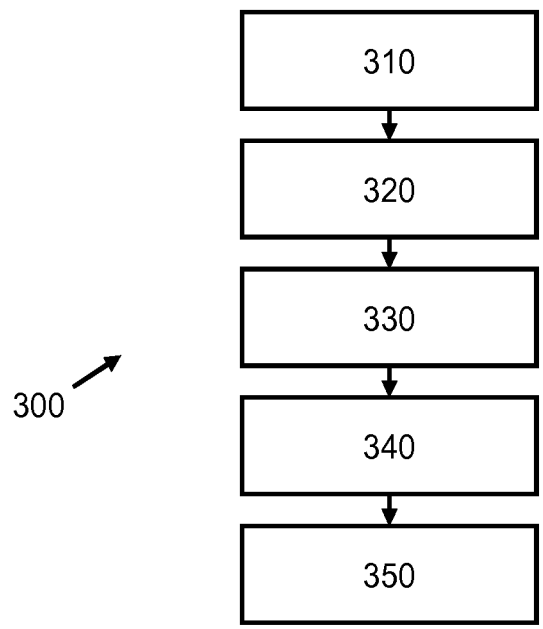
FIG. 4 shows a method for interactive mesh editing, in which a view is generated to intersect the 3D image substantially orthogonally to part of a mesh.

FIG. 4 shows a method 300 for interactive mesh editing, which may correspond to an operation of the system 100 as described with reference to FIG. 1.

The method 300 comprises, in an operation titled "ACCESSING IMAGE DATA", accessing 310 image data, the image data representing a three-dimensional image showing an anatomical structure. The method 300 further comprises, in an operation titled "OBTAINING MESH DATA", obtaining 320 mesh data, the mesh data defining a mesh which is mapped to the three-dimensional image for segmenting the anatomical structure. The method 300 further comprises, in an operation titled "RECEIVING USER INPUT DATA", receiving 330 user input data indicative of an editing action to be mapped to at least a part of the mesh shown in the view. The method 300 further comprises, in an operation titled "GENERATING VIEW", generating 340 a view of the three-dimensional image and the mapped mesh, wherein said generating is based on one or more viewing parameters defining the view, with said generating 340 the view comprising, as a sub-operation, establishing the one or more viewing parameters based on a local orientation of the part of the mesh. The method 300 further comprises, in an operation titled "GENERATING VIEW DATA", generating 350 view data representing the view for display on a display. Optionally, the method 300 may further comprise, in an operation titled "INTERACTIVE MESH EDITING", enabling a user to carry out the editing action in the generated view.

Figure 5:
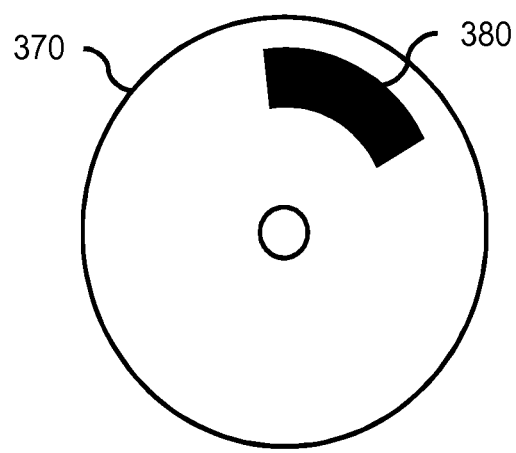
FIG. 5 shows a computer readable medium comprising instructions for causing a processor system to perform the method.

It will be appreciated that the above operation may be performed in any suitable order, e.g., consecutively, simultaneously, or a combination thereof, subject to, where applicable, a particular order being necessitated, e.g., by input/output relations. For example, the image data and mesh data may be obtained simultaneously or in any order. The method 300 may be implemented on a computer as a computer implemented method, as dedicated hardware, or as a combination of both. As also illustrated in FIG. 5, instructions for the computer, e.g., executable code, may be stored on a computer readable medium 370, e.g., in the form of a series 380 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 5 shows an optical disc 370.

It will be appreciated that, in accordance with the abstract of the present application, the provided system and method may enable the user to interactively edit a mesh which has been applied or mapped to a 3D image to segment an anatomical structure shown therein. To facilitate the interactive editing of the mapped mesh, a view of the 3D image may be generated which shows a mesh part to be edited, with the view being established based on a local orientation of the mesh part. Advantageously, the view may be generated to be substantially orthogonally to the mesh part, or to a centerline of the anatomical structure which is determined as a function of the mesh part. Accordingly, an orthogonal view may be established which facilitates the user in carrying out the editing action with respect to the mesh part. It may therefore not needed for the user to manually navigate through the 3D image to obtain a view which is suitable for mesh editing, which is typically time consuming.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for interactive mesh editing, comprising:
    an image data interface configured to access image data, the image data representing a three-dimensional image showing an anatomical structure;
    a processor configured for:
        obtaining mesh data, the mesh data defining a mesh which having been previously mapped to the three-dimensional image for segmenting the anatomical structure,
        generating a view of the three-dimensional image and said mapped mesh, wherein said generating is based on one or more viewing parameters defining the view, and
        generating view data representing the view for display on a display;
    a user input interface for receiving user input data indicative of an editing action to be mapped to at least a part of the mesh shown in the view;
    wherein the processor is configured for establishing the one or more viewing parameters based on a local orientation of the part of the mesh upon receiving the user input data indicative of the editing action,
    wherein the part of the mesh comprises a set of mesh surface elements, and wherein the processor is configured for determining the local orientation of the part of the mesh by applying a statistical function to the normal vectors of the mesh surface elements from the set of mesh surface elements,
    wherein the set of mesh surface elements is located within a radius of a reference mesh surface element,
    wherein the processor is configured for determining a difference between a) a result of the statistical function applied to the normal vectors of the mesh surface elements, and b) the normal vector of the reference mesh surface element, for omitting using the result of the statistical function as said determined local orientation if the difference exceeds a first predetermined threshold.

2. The system according to claim 1, wherein the processor is configured for establishing the one or more viewing parameters to define the view to intersect the three-dimensional image substantially orthogonally to the part of the mesh, thereby establishing an orthogonal view.

3. The system according to claim 2, wherein the processor is configured for, from an initial view showing the part of the mesh, switching to the orthogonal view upon receiving the user input data indicative of the editing action.

4. The system according to claim 3, wherein the processor is configured for effecting said switching if the initial view intersects the three-dimensional image parallel to the part of the mesh, or at an intersection angle below a predetermined angle.

5. The system according to claim 1, wherein the statistical function is an average or a median.

6. The system according to claim 1, wherein the processor is configured for, if the difference exceeds the first predetermined threshold:
- determining a subset of the set of mesh surface elements, the subset comprising mesh surface elements of which the normal vector deviates less than a second predetermined threshold from the result of the statistical function; and
- determining the local orientation of the part of the mesh by applying the statistical function to the normal vectors of the mesh surface elements from said subset.

7. The system according to claim 1, wherein the processor is configured for establishing the one or more viewing parameters to define the view to intersect the three-dimensional image substantially orthogonally to a centerline of the anatomical structure which is determined as a function of the location of the part of the mesh.

8. Workstation comprising the system according to claim 1.

9. Imaging apparatus comprising the system according to claim 1.

10. Method for interactive mesh editing, comprising:
- accessing image data, the image data representing a three-dimensional image showing an anatomical structure;
- obtaining mesh data, the mesh data defining a mesh which having been previously mapped to the three-dimensional image for segmenting the anatomical structure;
- receiving user input data indicative of an editing action to be applied to at least a part of the mesh shown in the view;
- generating a view of the three-dimensional image and the mapped mesh, wherein said generating is based on one or more viewing parameters defining the view;
- generating view data representing the view for display on a display; and
- wherein the generating the view comprises establishing the one or more viewing parameters based on a local orientation of the part of the mesh upon receiving the user input data indicative of the editing action,
- wherein the part of the mesh comprises a set of mesh surface elements, and wherein the processor is configured for determining the local orientation of the part of the mesh by applying a statistical function to the normal vectors of the mesh surface elements from the set of mesh surface elements,
- wherein the set of mesh surface elements is located within a radius of a reference mesh surface element,
- wherein the processor is configured for determining a difference between a) a result of the statistical function applied to the normal vectors of the mesh surface elements, and b) the normal vector of the reference mesh surface element, for omitting using the result of the statistical function as said determined local orientation if the difference exceeds a first predetermined threshold.

11. A non-transitory computer readable storage medium comprising a computer program product comprising instructions for causing a processor system to perform the method according to claim 10.

* * * * *